(12) United States Patent
Huemer

(10) Patent No.: US 9,283,313 B2
(45) Date of Patent: Mar. 15, 2016

(54) DEVICE AND FILTER CARTRIDGE FOR SEPARATING PLASMA FROM WHOLE BLOOD

(71) Applicant: Roche Diagnostics Operations, Inc., Indianapolis, IN (US)

(72) Inventor: Herfried Huemer, Feldbach (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/615,743

(22) Filed: Feb. 6, 2015

(65) Prior Publication Data

US 2015/0151035 A1    Jun. 4, 2015

Related U.S. Application Data

(63) Continuation of application No. PCT/EP2013/066539, filed on Aug. 7, 2013.

(30) Foreign Application Priority Data

Aug. 9, 2012 (EP) .................................... 12179900

(51) Int. Cl.
*A61M 1/36* (2006.01)
*G01N 1/14* (2006.01)
*G01N 33/49* (2006.01)
*B01L 3/00* (2006.01)

(52) U.S. Cl.
CPC .............. *A61M 1/3616* (2014.02); *B01L 3/502* (2013.01); *B01L 3/5635* (2013.01); *G01N 33/491* (2013.01); *B01L 3/5021* (2013.01); *B01L 2200/0621* (2013.01); *B01L 2300/0681* (2013.01); *B01L 2400/0478* (2013.01)

(58) Field of Classification Search
CPC .... A61M 1/3616; B01L 3/502; B01L 3/5635; G01N 33/491
See application file for complete search history.

(56) References Cited

U.S. PATENT DOCUMENTS 3,814,079 A * 6/1974 Le Roy, Sr. ................... 600/577
4,046,145 A   9/1977 Choksi et al.
4,131,549 A  12/1978 Ferrara
4,990,253 A   2/1991 Vcelka
(Continued)

FOREIGN PATENT DOCUMENTS

EP        0297441 A2    1/1989
EP        0550950 A2    7/1993
(Continued)

OTHER PUBLICATIONS

International Search Report issued Nov. 6, 2013 in Application No. PCT/EP2013/066539, 3 pages.

*Primary Examiner* — Krishnan S Menon
*Assistant Examiner* — Bradley R Spies
(74) *Attorney, Agent, or Firm* — Roche Diagnostics Operations, Inc.

(57) ABSTRACT

A multi-part device for separating plasma from whole blood is provided, with a sample taking unit for receiving whole blood, a filter unit with a layered filter with multiple layers for extracting plasma, and a pumping unit, typically a plunger pump, for creating a partial vacuum in the filter unit. The filter unit and a plasma collector vessel with a conical tip extending towards the filter unit are contained in a filter cartridge, which may be taken apart after plasma extraction, thus exposing the conical tip of the plasma collector vessel for sample input into an analyzer.

10 Claims, 2 Drawing Sheets

(56) References Cited

U.S. PATENT DOCUMENTS

| | | | |
|---|---|---|---|
| 5,074,312 A * | 12/1991 | Sarstedt | 600/577 |
| 5,234,608 A | 8/1993 | Duff | |
| 5,262,067 A | 11/1993 | Wilk et al. | |
| 5,336,412 A | 8/1994 | Huse et al. | |
| 5,364,533 A * | 11/1994 | Ogura et al. | 210/645 |
| 5,578,459 A * | 11/1996 | Gordon et al. | 135/29 |
| 5,637,087 A * | 6/1997 | O'Neil et al. | 604/82 |
| 5,919,356 A * | 7/1999 | Hood | 210/85 |
| 6,039,868 A | 3/2000 | Allen et al. | |
| 6,117,394 A * | 9/2000 | Smith | 422/513 |
| 6,669,905 B1 * | 12/2003 | Mathias et al. | 422/44 |
| 6,761,855 B1 | 7/2004 | Cook et al. | |
| 2002/0134175 A1 * | 9/2002 | Mehra et al. | 73/863.85 |
| 2002/0143298 A1 * | 10/2002 | Marsden | 604/190 |
| 2008/0015470 A1 * | 1/2008 | Sarstedt | 600/584 |
| 2010/0093551 A1 * | 4/2010 | Montagu | 506/7 |
| 2012/0118825 A1 * | 5/2012 | Margraf et al. | 210/645 |

FOREIGN PATENT DOCUMENTS

| | | |
|---|---|---|
| EP | 1469068 A1 | 10/2004 |
| WO | 94/25848 A1 | 11/1994 |
| WO | 96/24425 A1 | 8/1996 |
| WO | 2011/033000 A2 | 3/2011 |
| WO | 2012/062651 A1 | 5/2012 |

\* cited by examiner

DEVICE AND FILTER CARTRIDGE FOR SEPARATING PLASMA FROM WHOLE BLOOD

CROSS-REFERENCE TO RELATED APPLICATIONS

This application is a continuation of International Patent Application No. PCT/EP2013/066539, filed 7 Aug. 2013, which claims the benefit of European Patent Application No. 12179900.1 filed 9 Aug. 2012, the disclosures of which are hereby incorporated herein by reference in their entirety.

BACKGROUND

The present disclosure relates to a multi-part device for separating plasma from whole blood.

Besides centrifuges, which are used mainly in laboratories for separating plasma from whole blood, there are known a number of devices for obtaining very small amounts of plasma at the Point of Care (PoC) by separating plasma from whole blood by means of filtering.

In the simplest case plasma separation may be effected by means of a multilayer test strip as described in U.S. Pat. No. 5,262,067 A (BOEHRINGER MANNHEIM), where a transport layer on an inert carrier layer is provided for transporting sample fluid (whole blood) from an input area to a measuring area. The transport layer may for instance be made of glass fibre mat, which in the input area is covered by a plasma separation layer. The procedure is however only suitable for analysers processing test strips.

From EP 0 550 950 A2 (SANWA KAGAKU KENKYUSHO) there is known a method and a device for separating blood serum and plasma. This document presents diverse variants of devices for plasma extraction, where for instance in FIGS. 1 to 4 variants are described in which a plasma separating device is integrated in a blood sampler. By means of a partial vacuum blood is first sucked into a collector vessel in which there is disposed a two-layer separating filter.

After the blood sample has been taken the collector vessel is connected to an evacuated fluid container, the plasma being separated by the separating filter and collected in the fluid container. In the variant shown in FIGS. 5 and 6 the partial vacuum required for plasma separation is generated by means of a plunger syringe. The variant of FIGS. 9 and 10 furthermore shows a kind of syringe input filter, which may also be used for obtaining plasma.

From WO 96/24425 A1 (FIRST MEDICAL INC.), especially from its FIGS. 1 to 3 and 8, a method and device for plasma separation is known. A device called "Blood Separation Device" comprises a filter element, a flexible tube and at its end a needle which is introduced into a "Blood Collection Device". By means of a motor unit comprising a peristaltic pump acting on the flexible tube whole blood is sucked from the "Blood Collection Device" and pumped through the filter element, whereby plasma is separated and can be obtained for further use at a plasma output opening of the filter unit. The relatively high uncontrolled pressure values met at the filter unit when pressure is applied and the partial vacuum occurring in the collection vessel when whole blood is continuously sucked off are disadvantageous.

EP 1 469 068 A1 discloses an apparatus for separating and purifying nucleic acids, which comprises a cylindrical syringe having a leading end part in which a first opening part is formed, and an accommodation part being able to hold liquid therein. A solid phase-holding member is connected to the leading end part of the syringe and a flow hole is formed at the leading end side of the solid phase-holding member. A solid phase comprised of an organic polymer having a hydroxyl group on the surface thereof and being able to adsorb and desorb nucleic acids in a sample solution is accommodated in said solid phase-holding member. In the leading end part of the syringe there is formed a liquid-guiding surface of a shape that increases the diameter of the cross section towards the solid phase element. The apparatus can be used for separating and purifying nucleic acids but does not work as plasma separation device.

From U.S. Pat. No. 6,761,855 B1 an improved column for use in solid phase synthesis or purification of complex chemicals, such as biomolecules and more specifically oligonucleotides is known. The column has a top orifice with a sufficient diameter so that a fluid line or a multiple fluid line bundle may dispense fluids into the column with great efficiency. The column has an upper cavity portion configured and sized to render it compatible with dispensing pipettes, so that it can be used as a pipette tip to aspirate the column. The column has a lower cavity portion with a shoulder for ready placement of a lower frit to contain the solid support in a central cavity portion of the column. An upper frit can be conveniently placed in the central cavity portion to seal the solid phase resin. The lower end tip of the column is configured as a Luer-type fitting to provide a male Luer connection. The upper cavity portion is configured to interface with the male Luer of another column, so that two or more columns to be connected in series.

U.S. Pat. No. 4,046,145 B1 shows a connector for joining a small dose syringe to a large reservoir syringe for filling the small dose syringe from the reservoir syringe. The connector has a tubular female-to-female coupler and can be furnished with a filter element. Thus, particulate matter that might be within the large reservoir syringe is filtered out prior to its transfer to the small dose syringe.

It is an object of the present disclosure to propose a device for separating plasma from whole blood, which should be simple and economical to handle and where plasma samples for subsequent application steps may be obtained even from small blood samples and/or samples with high haematocrit values and where these samples may be fed to the input unit of an analyser in a simple way.

SUMMARY

It is against the above background that the present disclosure provides certain unobvious advantages and advancements over the prior art. In particular, the inventors have recognized a need for improvements in plasma separation systems and methods for plasma separation.

In accordance with one embodiment of the disclosure a multi-part device for separating plasma from whole blood is provided comprising a sample taking unit for receiving whole blood, a filter unit with a layered filter with multiple layers for extracting plasma, and a pumping unit, typically a plunger pump, for creating a partial vacuum in the filter unit. The disclosure further relates to a filter cartridge with a multi-layer filter unit for separating plasma from whole blood.

According to the disclosure this object is achieved by proposing that the filter unit and a plasma collector vessel with a conical tip extending towards the filter unit be contained in a filter cartridge, which is separable or may be taken apart after plasma extraction, thus exposing the conical tip of the plasma collector vessel for sample input into an analyser. The plasma collector vessel penetrates with its tip a seal towards the filter unit and is held on its opposite end by a supporting element, typically by a clamping seal, which has a passage leading to the pumping device, e.g., a plunger pump.

The seal towards the filter unit and the supporting element or clamping seal in the filter cartridge define a dead volume or compensation volume, which is connected via an air-permeable connection, for instance a compensation opening or a porous membrane, with the pumping device. In this way, the filter unit will not be subjected to pressure in an uncontrolled direct way (dependent on the handling of the plunger of the pumping unit) but slowly and with uniformly diminishing intensity, the pressure situation being determined by the geometry (e.g., the ratio between suction volume of the plunger pump and compensation volume in the filter cartridge) of the individual parts of the separation device and the characteristics of the filter element.

Typically the filter cartridge may be taken apart or separated by pulling, screwing or wrenching off the plasma applicator containing the plasma collector vessel with conical tip from the filter housing containing the filter unit. After plasma extraction and detaching of the plasma applicator, the plasma collector vessel with conical tip may by means of this tip be directly docked onto the input opening of an analyser, and the plasma sample obtained may be sucked into the analyser for subsequent analyte determination.

According to another embodiment of the disclosure, a filter cartridge with a multi-layer filter unit for extraction of plasma from whole blood is provided, the filter cartridge having in its interior a plasma collector vessel with a conical tip that penetrates a seal towards the filter unit and where the plasma collector vessel is held in the filter cartridge on its opposite end by a clamping seal. The filter cartridge may be disposed within or integrated or set in a syringe or a so-called Monovette. (Sarstedt AG & Co. Kommanditgesellschaft, having a location at Sarstedstraße 1, 51588 Nuembrecht, Germany, sells a line of blood collection devices under the registered trademark S-Monovette®.)

In accordance with one or more other embodiments of the disclosure, the collector vessel containing whole blood can be connected to a filter unit by introducing a suction tube and an aeration tube of the filter unit into the collector vessel. Also, the partial vacuum in the filtering device can be controlled by a control device of the analyser, typically by pressure dependent control of the flow rate of the suction pump.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
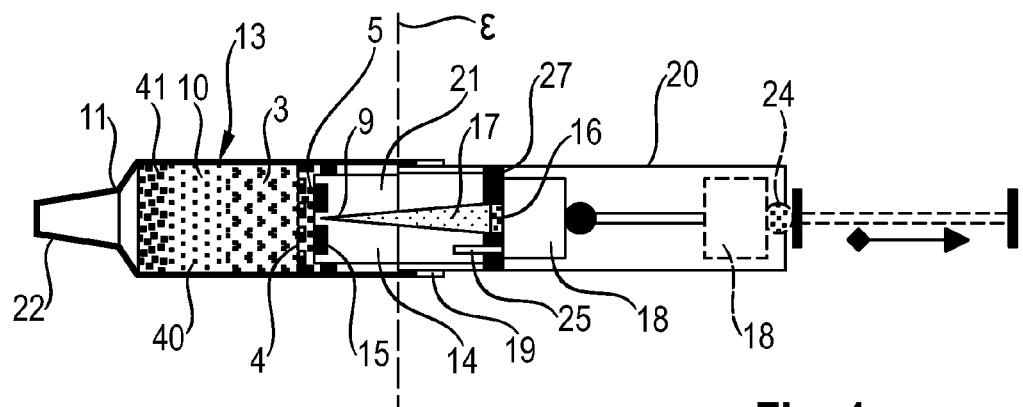
FIG. 1 is a first variant (syringe) of the device according to the disclosure for separating plasma from whole blood in sectional view.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

The various embodiments of the present disclosure have a filter cartridge 13 as a common element, either as an integral component of the sample taking unit (see syringe 11 of FIG. 1 or 3) or as a separate part, which is inserted by the user into a sample taking unit (see Monovette 12 of FIGS. 4 to 7). The filter cartridge 13 comprises a filter unit 10 with a multi-layered filter, and a plasma collector vessel 17 with a conical tip extending towards the filter unit 10 (plasma tip). The filter cartridge 13 may be separated or broken apart after plasma extraction along a plane ε, yielding a plasma applicator 14 containing the plasma collector vessel 17 and a filter housing 8 containing the filter unit 10.

Figure 2:
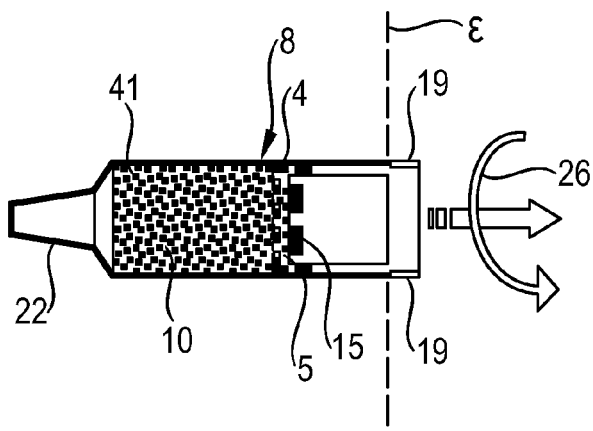
FIG. 2 is the first part of the device according to FIG. 1 after plasma extraction.
Figure 3:
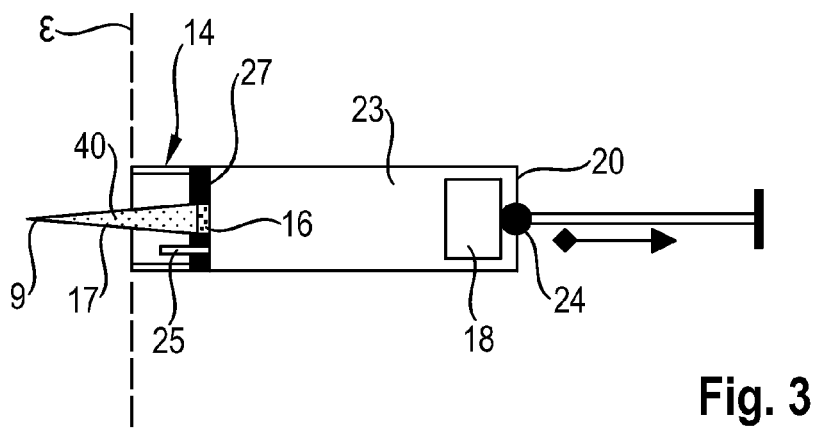
FIG. 3 is the second part of the device according to FIG. 1 after plasma extraction.

The first variant shown in FIGS. 1 to 3 has a filter cartridge 13 integrated in a syringe 11 with a Luer cone 22 formed on the filter housing 8, onto which a needle may be placed for taking a whole blood sample. In the housing of the syringe 11, in whose plunger housing 20 a plunger 18 is disposed that can be manually moved by means of a rod from an initial position to an end position indicated by a broken line, a filter unit 10 and a plasma collector vessel 17 with a conical tip extending towards the filter unit 10 are provided as the essential parts of the filter cartridge. The plunger housing 20 with the slideable plunger 18 serves as pumping device for creating the partial vacuum required for plasma separation.

On activation of the device the whole blood sample 41 is sucked into the filter unit 10 by pulling back the plunger 18, whereby a plasma front or plasma fraction 40 is generated, which moves into the tip 9 of the plasma collector vessel 17 through the multi-layered filter consisting of a deep-bed filter 3, a small-pore stop membrane 4 for complete removal of solid blood components (mainly red blood cells, RBCs) and a lateral grid 5.

The plasma collector vessel 17 with its tip 9 penetrates a seal 15 towards the filter unit 10 and is held and sealed on the opposite open end by a supporting element, typically by a clamping seal 27, which has a passage towards the pumping device (plunger part 20). In this passage towards the pumping device a hydrophobic, air-permeable element 16 (liquid stop) is provided. This will prevent the outflow of separated plasma through the passage opposite the tip 9.

The seal 15 towards the filter unit 10 and the clamping seal 27 towards the plunger housing 20 define a compensation volume 21 in the filter cartridge 13, which is connected to the pumping device of the syringe 11 via an air-permeable passage, for instance a compensation opening 25 in the clamping seal 27 or a porous membrane.

In a first variant of the device according to FIGS. 1 to 3 plasma extraction may be carried out as follows:

Taking the syringe 11 with integrated filter cartridge 13 from a sterile package.

Placing a needle onto the Luer cone 22.

Puncturing a selected blood vessel with the needle.

Sucking in a blood sample by pulling back the plunger 18 until it hits the stop.

Locking the plunger rod in a locking position 24.

(Option: the plunger rod may be broken off to avoid reversal of the internal flow direction or pressure fluctuations and any resulting contamination of the obtained plasma at high haematocrit values and/or small sample volume.)

The deep-bed filter 3 of the filter unit 10 may for instance be built up from glass fibers without binding agent (typically FV-2, Whatman Inc., resp. DE 40 15 589 A1, or EP 0 239 002 A1 Böhringer-Mannheim) with a retention range of 0.5 µm to 10 µm, typically 1 µm to 5 µm, more typically <3 µm. The red blood cells (RBCs) will collect on the thin glass fibers of the deep bed filter 3 without bursting or unduly influencing the rate of flow.

Depending on the cross-section of the filter unit 10 and on haematocrit a "plasma front" or "plasma fraction" 40 will form, which can pass the stop membrane 4 unimpededly. Residual RBCs not held back by the deep-bed filter are filtered out by the stop membrane 4. For this purpose the stop membrane 4 has a pore size significantly smaller than that of the deep-bed filter 3, i.e., pore diameters of less than 400 nm, typically less than 200 nm. By combining a deep-bed filter 3, which on account of its pore size already retains the greater part of blood cells but does not impede the flow of the plasma fraction, with a subsequent stop membrane 4, which due to its smaller pore size will reliably retain remaining blood cells, but would clog swiftly on account of its limited number of pores if the preceding deep-bed filter 4 were absent, a reliable separation of blood cells without clogging of the filter can be achieved, thus making it possible to obtain a sufficiently large volume of plasma sample.

The partial vacuum of not more than 500 mbar, typically 300 mbar, more typically 100 to 150 mbar, established in the filter unit 10, together with the geometry of the filter unit 10 (ratio of compensation volume 21 to suction volume 23 of the plunger housing 20) will determine the flow rate and thus the shear forces acting especially on the RBCs within the stop membrane 4 of the filter unit 10. Bursting of RBCs (haemolysis) can efficiently be prevented by optimizing the compensation volume 21.

The lateral grid 5 of the filter unit 10 permits plasma to be collected and sucked off behind the stop membrane 4 towards the plasma collector vessel 17 by efficiently preventing the stop membrane 4 from "sealing off" tightly. Due to its grid structure the lateral grid 5 on the one hand acts as a non-continuous support for the stop membrane 4, letting plasma flow out on the output side of the stop membrane 4. By forming channels the grid structure furthermore enables plasma that exits over the area of the stop membrane 4, to converge towards the plasma collector vessel 17.

(This functionality of the lateral grid 5 may alternatively be provided by structuring the side of the seal 15 facing the stop membrane, e.g., by stamping, or otherwise providing for sufficient roughness of its surface.)

Plasma extraction is also ended by:
when the stop membrane 4 is clogged by particulate components of blood, or
especially in the case of haematocrit values <40%, by a hydrophobic, air-permeable element 16 (liquid stop) at the end of the plasma collector vessel 17 or in the passage of the clamping seal 27, which terminates further plasma extraction when the lumen of the plasma collector vessel 17 bounded by the hydrophobic, air-permeable element 16 is completely filled with plasma.

By means of marks on the plasma collector vessel 17 one can optionally ascertain by visual inspection that the desired amount of plasma has been obtained.

The filter housing 8 of the syringe 11 (see arrow 26 in FIG. 2) is unscrewed from or wrenched off the plunger part 20 and thus the filter cartridge 13 is divided along a plane E into a first part containing the filter unit 10 and into a plasma applicator part 14 containing the plasma collector vessel 17 with conical tip, the tip 9 of the plasma collector vessel 17 thus being exposed (FIG. 3).

In the variant shown the inherently higher static friction of the clamping seal 27, as compared with the seal 15 of the plasma collector vessel 17 with its smaller sealing surface, will ensure safe undocking of the tip 9 of the plasma collector vessel 17 prior to the exposure of aeration channels 19 in the housing walls due to further turning or pulling-off of the housing, which channels will permit fast pressure compensation between the suction volume 23 in the plunger housing 20 and the compensation volume 21, either via the partly porous clamping seal 27 and/or via the compensation opening 25.

Early undocking will also ensure that unforeseen complications and contaminations do not occur at the tip 9 of the plasma collector vessel 17 during the separation procedure.

The liquid-stop 16 in the clamping seal 27 at the end of the plasma collector vessel 17 will also prevent fractionating of the plasma sample in the area at the point of tip 9 if pressure compensation between suction volume 23 and compensation volume 21 is retarded.

(Alternatively the tip 9 of the plasma collector vessel 17 may be designed as a Luer cone).

Docking the plasma collector vessel 17 (plus plunger housing 20 acting as a handle), which is at least partly filled with the plasma obtained, onto the input opening of an analyser not further shown here.

Entering the plasma sample into the analyser by sucking it, by analyser means, from the plasma collector vessel 17 that is docked onto the input opening of the analyser. The compensation opening 25 or, alternatively, the porous areas of the clamping seal 27 permit total drainage of the plasma collector vessel 17.

Analytic determination of the substances contained in the plasma sample obtained according to the present disclosure, for instance the haemoglobin values, in the analyser.

Figure 5:
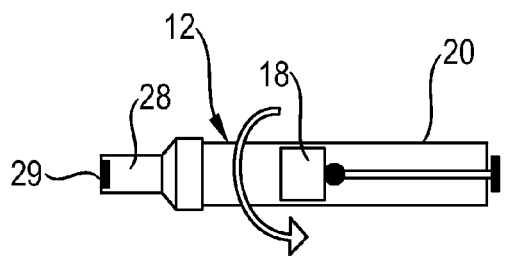
FIG. 5 is a Monovette for plasma extraction according to FIG. 4.
Figure 6:
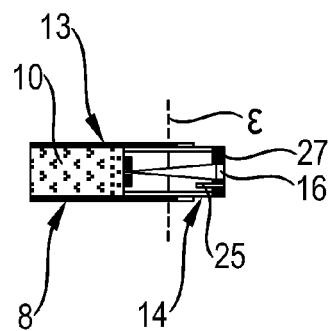
FIG. 6 is a filter cartridge according to the disclosure for separating plasma from whole blood, to be inserted into a Monovette according to FIG. 5.

In a second variant of the device according to FIGS. 4 to 7 plasma extraction may be carried out as follows:

Taking a Monovette 12 as in FIG. 5 from a sterile package.

Unscrewing the adapter cap 28 with puncturing membrane 29 from the plunger housing 20.

Figure 4:
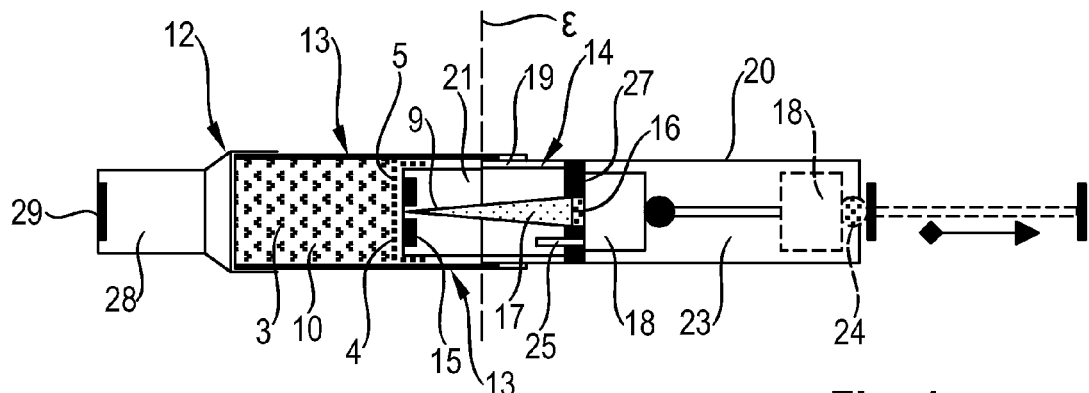
FIG. 4 is a second variant (Monovette) of the device according to the disclosure for separating plasma from whole blood in sectional view.

Placing the filter cartridge 13 between adapter cap 28 and plunger housing 20 according to FIG. 4.

Creating a partial vacuum in the Monovette 12 by pulling back the plunger 18 until it meets the stop, locking the plunger rod in locking position 24 shown in broken lines.

(Optionally: breaking off the plunger rod to avoid reversal of internal flow direction).

Docking the puncturing membrane 29 of the adapter cap 28 onto a puncturing needle, e.g., butterfly.

Sucking in the blood sample by means of the partial vacuum prevalent in the Monovette 12.

The deep-bed filter 3 of the filter unit 10 may for instance be built up from glass fibers without binding agent (typically FV-2, Whatman Inc., resp. DE 40 15 589 A1, or EP 0 239 002

A1, Böhringer-Mannheim) with a retention range of 0.5 µm to 10 µm, typically 1 µm to 5 µm, more typically <3 µm. The red blood cells (RBCs) will collect on the thin glass fibers of the deep bed filter 3 without bursting or unduly influencing the rate of flow.

Depending on the cross-section of the filter unit 10 and on haematocrit a "plasma front" or "plasma fraction" 40 will form, which can pass the stop membrane 4 unimpededly. Residual RBCs not held back by the deep-bed filter are filtered out (FIG. 4) by the stop membrane 4. For this purpose the stop membrane 4 has a pore size significantly smaller than that of the deep-bed filter 3, i.e., pore diameters of less than 400 nm, typically less than 200 nm. By combining a deep-bed filter 3, which on account of its pore size already retains the greater part of blood cells, but does not impede the flow of the plasma fraction, with a subsequent stop membrane 4, which due to its smaller pore size will reliably retain remaining blood cells, but would clog swiftly on account of its limited number of pores if the preceding deep-bed filter 4 were absent, a reliable separation of blood cells without clogging of the filter can be achieved, thus making it possible to obtain a sufficiently large volume of plasma sample.

The partial vacuum of not more than 500 mbar, typically 300 mbar, more typically 100 to 150 mbar, established in the filter unit 10, together with the geometry of the filter unit 10 (ratio of compensation volume 21 to suction volume 23 of the plunger housing 20), will determine the flow rate and thus the shear forces acting especially on the RBCs within the stop membrane 4 of the filter unit 10. Bursting of RBCs (haemolysis) can efficiently be prevented by optimizing the compensation volume 21.

The lateral grid 5 of the filter unit 10 permits plasma to be collected and sucked off behind the stop membrane 4 towards the plasma collector vessel 17, by efficiently preventing the stop membrane 4 from "sealig off" tightly (see also the syringe variant).

(As an alternative, this functionality of the lateral grid 5 may be provided by structuring the side of seal 15 facing the stop membrane, e.g., by stamping, or otherwise providing for sufficient roughness of its surface.)

Plasma extraction is also ended by:
when the stop membrane 4 is clogged by particulate components of blood, or
especially in the case of haematocrit values <40% by a hydrophobic, air-permeable element 16 (liquid stop) at the end of the plasma collector vessel 17 or in the passage of the clamping seal 27, which terminates further plasma extraction when the lumen of the plasma collector vessel 17 bounded by the hydrophobic, air-permeable element 16 is completely filled with plasma.

By means of marks on the plasma collector vessel 17 one can once again ascertain by visual inspection that the desired amount of plasma has been obtained.

Figure 7:
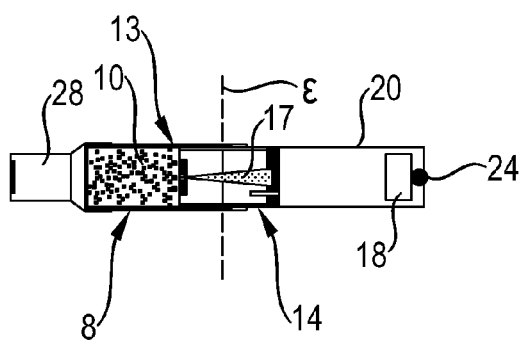
FIG. 7 is the filter cartridge of FIG. 6 inserted into the Monovette of FIG. 5 in a sectional view.

The front part of the Monovette 12 is unscrewed from or wrenched off the plunger part 20 and thus the interposed filter cartridge 13 is divided along a plane ϵ in a filter housing 8 containing the filter unit 10 and in a plasma applicator part 14 containing the plasma collector vessel 17 with conical tip, the tip 9 of the plasma collector vessel 17 thus being exposed (FIG. 7). The plasma applicator 14 remains connected to the filter housing 20 for ease of handling. After the parts have been separated the device corresponds to that of FIG. 3.

The further steps of the procedure correspond to those described in the first variant of the device according to the disclosure.

It is noted that terms like "preferably", "commonly" and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these preferred aspects.

What is claimed is:

1. A multi-part device for separating plasma from whole blood, comprising:
    a sample taking unit for receiving whole blood,
    a filter unit with a layered filter with multiple layers for extracting plasma, and
    a pumping unit having a plunger for creating a partial vacuum in the filter unit, wherein
        the filter unit and a plasma collector vessel having a conical tip extending towards the filter unit are contained in a filter cartridge,
        the conical tip of the plasma collector vessel penetrates a seal towards the filter unit and the collector vessel is held on its opposite end by a supporting element, which has a hydrophobic, air-permeable passage that leads to the pumping device and that prevents the outflow of separated plasma from the plasma collector vessel,
        the filter cartridge is separable after plasma extraction, thus exposing the conical tip of the plasma collector vessel for sample input into an analyser, and
        the volume between the seal towards the filter unit and the supporting element defines a compensation volume of the filter cartridge that is separate from the plasma interior volume of the collector vessel and wherein the compensation volume of the filter cartridge is connected to the pumping device via an air-permeable connection,
        wherein both the interior volume of the plasma collector vessel and the compensation volume are in air communication via the hydrophobic, air-permeable passage and the air-permeable connection when the plunger is displaced from the supporting element forming a suction volume to create the partial vacuum in the filter unit.

2. The device according to claim 1, wherein the supporting element is a clamping seal.

3. The device according to claim 1, wherein the air-permeable connection is a compensation opening or a porous membrane.

4. The device according to claim 1, wherein the filter cartridge is separable by pulling, screwing or wrenching off a plasma applicator containing the plasma collector vessel with its conical tip from the filter housing that contains the filter unit.

5. The device according to claim 1, wherein the multi-layer layered filter of the filter unit comprises a deep-bed filter, a stop membrane and a lateral grid.

6. The device according to claim 1, wherein the filter cartridge is disposed or integrated in a plunger syringe or is insertable into said syringe.

7. The device according to claim 6, wherein the plunger of the syringe in its initial position prior to plasma extraction rests against the supporting element of the filter cartridge and at the end of plasma extraction locks into a locking position.

8. A filter cartridge with a multi-layer filter unit for extracting plasma from whole blood, wherein the filter cartridge in its interior has a conical plasma collector vessel, whose tip penetrates a seal towards the filter unit, the plasma collector vessel being held at its other end in the filter cartridge by a supporting element which has a hydrophobic air-permeable passage leading to a connectable pumping device, and wherein the volume between the seal and the supporting element defines a compensation volume of the filter cartridge that is separate from the interior volume of the plasma collector vessel and wherein the compensation volume of the filter cartridge is also connectable to the pumping device via an air-permeable connection.

9. The filter cartridge according to claim 8, wherein the supporting element is a clamping seal.

10. The filter cartridge according to claim 8, wherein the filter cartridge is separable by pulling off, wrenching off or screwing off a plasma applicator containing the conical plasma collector vessel from a filter housing containing the filter unit, thus exposing the tip of the plasma collector vessel for sample input into an analyser.

* * * * *